United States Patent
Toida

(10) Patent No.: US 6,680,779 B2
(45) Date of Patent: Jan. 20, 2004

(54) OPTICAL TOMOGRAPH

(75) Inventor: Masahiro Toida, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 207 days.

(21) Appl. No.: 09/841,484

(22) Filed: Apr. 25, 2001

(65) Prior Publication Data

US 2002/0003607 A1 Jan. 10, 2002

(30) Foreign Application Priority Data

Apr. 26, 2000 (JP) ........................... 2000/126180

(51) Int. Cl.[7] .................................. G01B 9/02
(52) U.S. Cl. ................. 356/479; 356/477; 356/497
(58) Field of Search .................... 356/479, 497, 356/477, 478, 480, 481, 482, 483

(56) References Cited

U.S. PATENT DOCUMENTS

| | | |
|---|---|---|
| 5,291,267 A | 3/1994 | Sorin et al. |
| 5,459,570 A * | 10/1995 | Swanson et al. ............ 356/479 |
| 6,212,000 B1 * | 4/2001 | Ishikawa .................. 359/124 |

FOREIGN PATENT DOCUMENTS

| | | |
|---|---|---|
| EP | 0 527 265 A1 | 2/1993 |
| EP | 0 586 713 A1 | 3/1994 |
| WO | WO 99/46557 | 9/1999 |

OTHER PUBLICATIONS

Science; vol. 254; Optical Coherence Tomography by David Huang, et al; Nov. 1991; pp. 1178–1181.
D. Huang, et al.; "Optical Coherence Tomography" Science, American Association for the advancement of science; vol. 254; No. 5035; Nov. 22, 1991.

* cited by examiner

Primary Examiner—Euncha Cherry
(74) Attorney, Agent, or Firm—Sughrue Mion, PLLC

(57) ABSTRACT

An optical tomograph obtains a tomogram of an object by dividing a low coherence light beam into a signal light beam and a reference light beam, shifting the frequency of at least one of the signal light beam and the reference light beam so that the signal light beam and the reference light beam becomes different from each other in frequency, causing the signal light beam to impinge upon the object, causing the signal light reflected at a predetermined depth of the object to interfere with the reference light beam, and measuring the intensity of the obtained interference light. A light amplifier amplifies the reflected signal light.

13 Claims, 2 Drawing Sheets

OPTICAL TOMOGRAPH

BACKGROUND OF THE INVENTION

1. Field of the Invention

This invention relates to an optical tomograph for obtaining an optical tomogram of an object by projecting low coherence signal light beam onto the object, and more particularly to an optical tomograph which images the fine structure of the surface and a deep portion of the object on the basis of the reflected signal light.

2. Description of the Related Art

In order to obtain, for instance, an optical tomogram representing a fine structure under the eye ground retina, there has been used an optical tomograph employing low coherence light, that is, an optical tomograph which obtains an optical tomogram of an object by measuring intensity of low coherence interference light by heterodyne detection.

For example, in "Science, No. 254, pp. 1178 to 1181" by D. Haung et. al., there has been proposed an optical tomograph which obtains a tomogram of an object by dividing a low coherence light beam emitted from a light source which may comprise, for instance, a SLD (super luminescent diode) into a signal light beam and a reference light beam, causing the signal light beam to impinge upon an organic object while slightly shifting the frequency of the reference light beam by a piezoelectric element of the like, causing the signal light beam reflected at a depth of the object to interfere with the frequency-shifted reference light beam, and measuring intensity of the obtained interference light by heterodyne detection. In the optical tomograph, an optical tomogram at a depth at which the optical path length of the signal light beam conforms to that of the reference light beam is obtained. Accordingly, by changing the optical path length of the reference light beam by moving a movable mirror provided on the optical path of the reference light beam, the depth at which the tomogram is obtained can be changed.

However, in such an optical tomograph, the optical output of the light source is conventionally limited so that the intensity of the signal light beam does not exceed a specified value not to adversely affect the organism. Since the intensity of the signal light beam is limited, the intensity of the reflected signal light beam becomes further low. As a result, the S/N of the image data obtained becomes unsatisfactory.

SUMMARY OF THE INVENTION

In view of the foregoing observations and description, the primary object of the present invention is to provide an optical tomograph in which image data which is excellent in S/N can be obtained with the intensity of the signal light beam held at a low level sufficient to ensure safety of the object.

In accordance with the present invention, there is provided an optical tomograph which obtains a tomogram of an object by dividing a low coherence light beam into a signal light beam and a reference light beam, shifting the frequency of at least one of the signal light beam and the reference light beam so that the signal light beam and the reference light beam becomes different from each other in frequency, causing the signal light beam to impinge upon the object, causing the signal light reflected at a predetermined depth of the object to interfere with the reference light beam, and measuring the intensity of the obtained interference light, wherein the improvement comprises a light amplifier which amplifies said reflected signal light.

The expression "shifting the frequency of at least one of the signal light beam and the reference light beam so that the signal light beam and the reference light beam becomes different from each other in frequency" means to shift the frequency of at least one of the signal light beam and the reference light beam so that there is generated such a frequency difference between the signal light beam and the reference light beam as to produce a beat signal, which alternately becomes strong and weak at a frequency equal to the frequency difference, when the signal and reference light beams are caused to interfere with each other.

Further, "the signal light reflected at a predetermined depth of the object" includes signal light reflected at the predetermined depth of the object and signal light reflected at the surface of the object.

The expression "measuring the intensity of the obtained interference light" means to measure the intensity of the beat signal (the interference light) which alternately becomes strong and weak, for instance, by heterodyne detection.

Preferably the light amplifier is a light amplifier with an optical waveguide.

The light amplifier with an optical waveguide may be any light amplifier so long as it is provided with an optical waveguide. That is, the light amplifier with an optical waveguide may be, for instance, a semiconductor light amplifier, a stimulated Raman light amplifier or an optical fiber light amplifier. Among those, the optical fiber light amplifier is especially preferred.

In the optical fiber light amplifiers, those having an optical fiber added with at least one ion selected from the group consisting of transition metal ions, rare earth element ions and complex ions are preferred.

As the transition metal ion, $Ti^{4+}$, $Cr^{3+}$, $Mn^{4+}$, $Mn^{2+}$ and $Fe^{3+}$ are preferred. As the rare earth element ions, $Sc^{3+}$, $Y^{3+}$, $La^{3+}$, $Ce^{3+}$, $Pr^{3+}$, $Nd^{3+}$, $Pm^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$ and $Lu^{3+}$ are preferred. As the complex ions, $WO_4^{2-}$, $MoO_4^{2-}$, $VO_4^{3+}$, $Pt(CN)_4^{2-}$ and $WO_6^{6-}$ are preferred.

As the optical fiber light amplifiers, those having an optical fiber added with pigment may be also suitably used.

When the object is a part of an organic body, the low coherence light beam is preferred to be from 600 nm to 1700 nm inclusive in wavelength.

In the optical tomograph in accordance with the present invention, since the reflected signal light is caused to interfere with the reference light after amplified by the light amplifier, optical tomographic image data higher in S/N can be obtained without increasing the intensity of the signal light beam to be projected onto the object to such a level as can adversely affect the safety of the object. Further, by amplifying reflected signal light reflected at such a depth of an organic body that it is impossible for the conventional optical tomograph to obtain tomographic image data, it becomes possible to detect interference light of the reflected signal light and the reference light, and accordingly, the optical tomograph of the present invention can obtain an optical tomogram at a larger depth.

When the light amplifier is provided with an optical waveguide, the light amplifier can be more easily inserted into the optical path of the reflected signal light. Especially when the light amplifier is an optical fiber light amplifier, the optical fiber for amplifying the reflected signal light can be rolled and accordingly the optical fiber can be long enough to amplify the reflected signal light to a desired level without substantially enlarging the light amplifier. Further, since being very low in noise, the optical fiber light amplifier can accurately amplify weak reflected signal light.

Further, when the optical fiber is added with at least one ion selected from the group consisting of transition metal ions, rare earth element ions and complex ions, the reflected signal light can be amplified at a high amplification factor in a desired wavelength band.

Transition metal ions, $Ti^{4+}$, $Cr^{3+}$, $Mn^{4+}$, $Mn^{2+}$ and $Fe^{3+}$, rare earth element ions, $Sc^{3+}$, $Y^{3+}$, $La^{3+}$, $Ce^{3+}$, $Pr^{3+}$, $Nd^{3+}$, $Pm^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$ and $Lu^{3+}$ and complex ions, $WO_4^{2-}$, $MoO_4^{2-}$, $VO_4^{3+}$, $Pt(CN)_4^{2-}$ and $WO_6^{6-}$ are easy to add to the optical fiber and accordingly, the optical fiber light amplifier manufacturing cost, that is, the optical tomograph manufacturing cost, can be lowered by the use of these ions.

When the optical fiber is added with pigment, reflected signal light in a desired wavelength band can be efficiently amplified.

An organic body exhibits optimal transitivity and scattering properties to a low coherence light beam which is from 600 nm to 1700 nm in wavelength.

DESCRIPTION OF THE PREFERRED EMBODIMENTS

Figure 1:
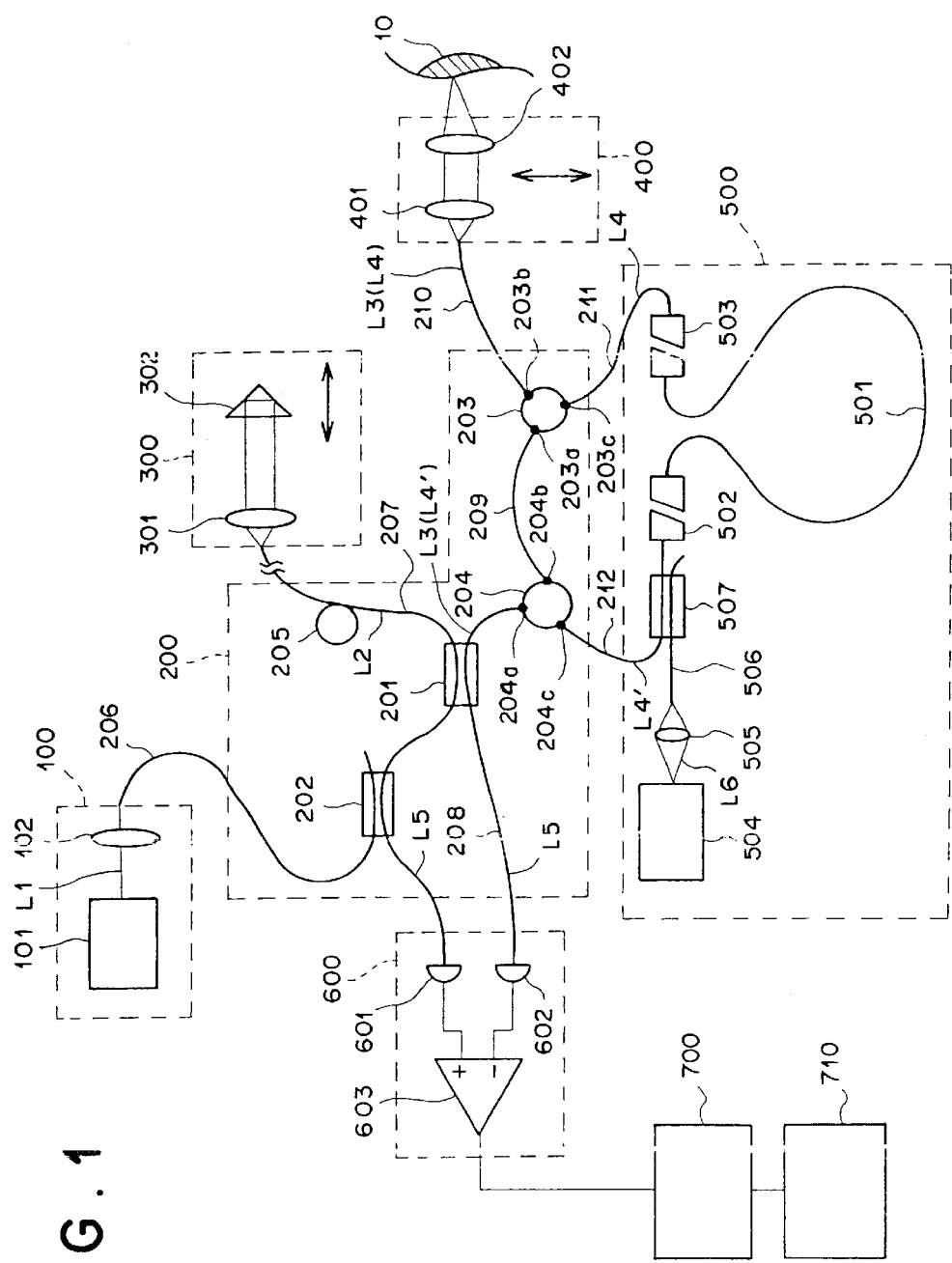
FIG. 1 is a schematic view showing an optical tomograph in accordance with a first embodiment of the present invention.

In FIG. 1, an optical tomograph in accordance with a first embodiment of the present invention comprises a light source system 100 which emits a low coherence light beam L1, a fiber optical coupling system 200 which divides the low coherence light beam L1 emitted from the light source system 100 into a reference light beam L2 and a signal light beam L3, and couples the reference light beam L2 with the reflected signal light beam reflected at an object as will be described in detail later, an optical path changing system 300 which changes the optical path length of the reference light beam L2, a scanning system 400 which causes the signal light beam L3 to scan an organic object 10, an optical fiber amplifier system 500 which amplifies the reflected signal light beam L4 (the signal light beam L3 reflected at a predetermined depth in the object 10) and emits amplified reflected signal light beam L4', a balancing difference detecting system 600 which detects the intensity of interference light beam L5 formed by the amplified reflected signal light beam L4' and the reference light beam L2, a signal processing system 700 which carries out heterodyne detection for obtaining the intensity of the reflected signal light beam L4 (the signal light beam L3 reflected at the predetermined depth in the object 10) on the basis of the intensity of the interference light beam L5 as detected by the balancing difference detecting system 600 and converts the intensity of the reflected signal light beam L4 into an image signal, and an image processing system 710 which reproduces a tomogram on the basis of the image signal obtained by the signal processing system 700.

The light source system 100 comprises a SLD (super luminescent diode) 101 which emits the low coherence light beam L1 which is 780 nm in central wavelength and 20 nm in spectral width, and a condenser lens 102 which condenses the low coherence light beam L1 emitted from the SLD 101.

The fiber optical coupling system 200 comprises a first fiber optic coupler 201 which divides the low coherence light beam L1 emitted from the light source system 100 into the reference light beam L2 and the signal light beam L3, and couples the reference light beam L2 with the reflected signal light beam L4 to obtain the interference light beam L5, a second fiber optic coupler 202 disposed between the light source system 100 and the first fiber optic coupler 201, a first optical circulator 203 which has three (first to third) ports 203a, 203b and 203c and transmits a light beam from one port to another, a second optical circulator 204 which has three (first to third) ports 204a, 204b and 204c and transmits a light beam from one port to another and a piezo-element 205 which slightly shifts the frequency of the reference light beam L3. The light source system 100 and the second fiber optic coupler 202 are connected by an optical fiber 206. The optical path changing system 300 is connected to one of two inputs of the balancing difference detecting system 600 by an optical fiber 207 with the first and second fiber optic couplers 201 and 202 connected between the optical path changing system 300 and the balancing difference detecting system 600. The piezo-element 205 is connected to the optical fiber 207. The second optical circulator 204 is connected to the other input of the balancing difference detecting system 600 by an optical fiber 208 with the first fiber optic coupler 201 connected there between. The first and second optical circulators 203 and 204 are connected to each other by an optical fiber 209. The first optical circulator 203 is connected to the scanning system 400 by an optical fiber 210 and to the optical fiber amplifier system 500 by an optical fiber 211. The second optical circulator 204 is connected to the optical fiber amplifier system 500 by an optical fiber 212. The optical fibers 206 to 211 are all of single mode.

The optical path changing system 300 comprises a collimator lens 301 and a movable prism 302. The collimator lens 301 collimates the reference light beam L2 emanating from the optical fiber 207 and causes the collimated reference light beam L2 to enter the prism 302, and at the same time, the collimator lens 301 causes the reference light beam L2 reflected by the prism 302 to enter the optical fiber 207. The prism 302 is movable in the horizontal direction and the optical path length of the reference light beam L2 by moving the prism 302 left and right.

The scanning system 400 comprises a pair of lenses 401 and 402 which are movable up and down and causes the reflected signal light beam L4 to enter the optical fiber 210.

The optical fiber amplifier system 500 comprises a fiber optic amplifier 501 which amplifies a light beam input into the amplifier 501 when it is in an excited state, a pair of optical fiber connectors 502 and 503 connected at opposite ends of the amplifier 501, an YAG laser 504 which emits an exciting light beam L6 (second harmonic at a wavelength of 532 nm) for the fiber optic amplifier 501, a condenser lens 505 which condenses the exciting light beam L6 emitted from the YAG laser 504, an optical fiber 506 which introduces the exciting light beam L6 into the optical fiber 212 by way of a fiber optic coupler 507. The fiber optic amplifier 501 comprises an optical fiber whose core is added with $Ti^{4+}$ having gain near to 780 nm and is rolled.

The balancing difference detecting system 600 comprises a pair of photodetectors 601 and 602 which detect the intensity of the interference light beam L5 and a differential amplifier 603 which adjusts input balance of the detecting values of the photodetectors 601 and 602 to cancel the noise component and the drift component and amplifies the difference.

Operation of the optical tomograph in accordance with this embodiment will be described, hereinbelow. The low coherence light beams L1 at a wavelength of 780 nm emitted from the SLD 101 is condensed by the lens 102 and caused to enter the optical fiber 206.

The low coherence light beam L1 travels through the optical fiber 206, and is introduced into the optical fiber 207 by the second fiber optic coupler 202, and is divided into a reference light beam L2 which travels toward the optical path changing system 300 through the optical fiber 207 and a signal light beam L3 which travels toward the second optical circulator 204 through the optical fiber 208.

The reference light beam L2 is modulated by the piezo-element 205 so that a slight frequency difference $\Delta f$ is generated between the reference light beam L2 and the signal light beam L3.

The signal light beam L3 enters the second optical circulator 204 through the first port 204a thereof and is introduced into the optical fiber 209 through the second port 204b. Then the signal light beam L3 enters the first optical circulator 203 through the first port 203a thereof and is introduced into the optical fiber 210 through the second port 203b. Thereafter the signal light L3 is caused to impinge upon the object 10 through the lenses 401 and 402 of the scanning system 10.

The part of the signal light beam L3 reflected at a predetermined depth of the object 10, i.e., the reflected signal light beam L4 returns to the optical fiber 210 through the lenses 401 and 402. Then the reflected signal light beam L4 enters the first optical circulator 203 through the second port 203b of the first optical circulator 203 and is introduced into the optical fiber 211 through the third port 203c. Then the reflected signal light beam L4 is introduced into the optical fiber amplifier system 500 and is amplified into an amplified reflected signal light beam L4' as will be described in more detail later. The amplified reflected signal light beam L4' is returned to the optical fiber 207 at the first fiber optic coupler 201 and is coupled to the reference light beam L2.

On the other hand, the reference light beam L2 modulated by the piezo-element 205 travels through the optical fiber 207, impinges upon the prism 302 through the lens 301 and is reflected by the prism 302 to return to the optical fiber 207. Then the reference light beam L2 is coupled with the amplified reflected signal light beam L4' by the first fiber optic coupler 201.

The reference light beam L2 and the amplified reflected signal light beam L4' are coaxially superimposed with each other and interfere with each other under a certain condition to form an interference light beam L5, which is a beat signal.

That is, since the reference light beam L2 and the amplified reflected signal light beam L4' are low coherence light beams which are short in coherence length, the reference light beam L2 and the amplified reflected signal light beam L4' interfere with each other when the optical path length between the point at which the low coherence light beam L1 is divided into the reference light beam L2 and the signal light beam L3 and the point at which the amplified reflected signal light beam L4' reaches the first fiber optic coupler 201 is equalized to the optical path length between the point at which the low coherence light beam L1 is divided into the reference light beam L2 and the signal light beam L3 and the point at which the reference light beam L2 reaches the first fiber optic coupler 201, and a beat signal, which alternately becomes strong and weak at a frequency equal to the frequency difference $\Delta f$ between the reference light beam L2 and the amplified reflected signal light beam L4', is generated.

The interference light beam L5 thus formed is divided into first and second parts by the first fiber optic coupler 201. The first part of the interference light beam L5 is input into the first photodetector 601 of the balancing difference detecting system 600 through the optical fiber 207 and the second part of the interference light beam L5 is input into the second photodetector 602 of the balancing difference detecting system 600 through the optical fiber 208.

Each of the first and second photodetectors 601 and 602 detects the intensity of the interference light L5 and the differential amplifier 603 obtains the difference between the detecting values of the first and second photodetectors 601 and 602 and outputs it to the signal processing system 700. Since the differential amplifier 603 has a function to adjust the balance of direct current components of the detecting values of the photodetectors 601 and 602, the differential amplifier 603 can detect only the beat signal component with the drift component cancelled even if the low coherence light beam L1 emitted from the light source system 100 includes a drift component.

The signal processing system 700 carries out heterodyne detection for obtaining the intensity of the reflected signal light beam L4 (the signal light beam L3 reflected at the predetermined depth in the object 10) on the basis of the intensity of the interference light beam L5 as detected by the balancing difference detecting system 600 and converts the intensity of the reflected signal light beam L4 into an image signal, and an image processing system 710 reproduces a tomogram on the basis of the image signal obtained by the signal processing system 700.

When the prism 302 of the optical changing system 300 is moved left and right, the optical path length of the reference light beam L2 changes and the depth of the object at which optical tomographic image data is obtained is changed.

By repeating the aforesaid procedure while changing the optical path length of the reference light beam L2, optical tomographic image data from the surface of the object 10 to a desired depth of the same at a desired point of the object 10 is obtained. Thereafter, the incident point of the signal light beam L3 to the object 10 is slightly moved up and down by the lenses 401 and 402 of the scanning system 400 and optical tomographic image data from the surface of the object 10 to the desired depth of the same at the point of the object 10 is obtained. In this manner, a tomogram of the object 10 can be obtained.

Operation of the optical fiber amplifier system 500 will be described here. The exciting light beam L6 at 532 nm emitted from the YAG laser 504 is condensed by the lens 505 and introduced into the optical fiber 506. The exciting light beam L6 is further introduced into the optical fiber 212 at the fiber optic coupler 507 and is introduced into the fiber optical amplifier 501 by way of the optical fiber connector 502. The exciting light beam L6 is absorbed by the $Ti^{4+}$ ions added to the core of the fiber optic amplifier 501 while it is propagating through the fiber optic amplifier 501. By absorbing the exciting light beam L6, the $Ti^{4+}$ ions shift from a ground state to an excited state. When the reflected signal light beam L4 enters the fiber optic amplifier 501 through one end thereof and propagates through the fiber optic amplifier 501 in the excited state, light in the same phase as the reflected signal light beam L4 is emitted in stimulated emission and the $Ti^{4+}$ ions return to the ground state. Such stimulated emission is repeated and amplified reflected signal light beam L4' is emitted through the other end of the fiber optic amplifier 501. That is, since the amplified reflected signal light beam L4' is a signal in the same phase as the reflected signal light beam L4, optical tomographic image data can be obtained from the interference light beam L5 obtained by causing the reference light beam L2 and the amplified reflected signal light beam L4' to interfere with each other.

By thus amplifying the reflected signal light beam L3 and measuring the intensity of the interference light beam L5 obtained by causing the amplified reflected signal light beam L4' to interfere with the reference light beam L2, optical tomographic image data higher in S/N can be obtained without increasing the intensity of the signal light beam to be projected onto the object to such a level as can adversely affect the safety of the object. Further, by amplifying the reflected signal light beam L3 reflected at such a depth of the object 10 that it is impossible for the conventional optical tomograph to obtain tomographic image data, it becomes possible to detect interference light L5 of the reflected signal light L4 beam and the reference light beam L2, and accordingly, the optical tomograph of the present invention can obtain an optical tomogram at a larger depth.

Further, in this particular embodiment, since the amplifier system 500 comprises a fiber optic amplifier 501, the optical fiber can be long enough to amplify the reflected signal light beam L4 to a desired level without substantially enlarging the light amplifier by rolling the optical fiber. Further, since being very low in noise, the fiber optic amplifier 501 can accurately amplify weak reflected signal light beam L4.

Further, in this particular embodiment, the fiber optic amplifier 501 is added with $Ti^{4+}$, and accordingly, the reflected signal light beam L4 at a wavelength near 780 nm can be effectively amplified.

Since an organic body generally exhibits optimal transitivity and scattering properties to a low coherence light beam which is from 600 nm to 1700 nm in wavelength, and in this particular embodiment, the signal light beam L3 is 780 nm in wavelength, a desirable optical tomogram of an organic body can be obtained in this embodiment.

In place of the SLD 101 which emits light at a wavelength of 780nm, an SLD which emits light at a wavelength of 1550 nm may be used. In this case, when an optical fiber added with $Er^{3+}$ is employed in the amplifier system 500 and a semiconductor laser emitting light at a wavelength of 980 nm is employed in place of the YAG laser 502 emitting light at a wavelength of 532 nm, the exciting light is absorbed by the $Er^{3+}$ ions and the reflected signal light of 1550 nm can be effectively amplified.

According to the wavelength band of the low coherence light beam L1, the ion to be added to the optical fiber of the fiber optic amplifier may be selected from the group consisting of transition metal ions, rare earth element ions and complex ions. As the transition metal ion, $Ti^{4+}$, $Cr^{3+}$, $Mn^{4+}$, $Mn^{2+}$ and $Fe^{3+}$ are preferred. As the rare earth element ions, $Sc^{330}$, $Y^{3+}$, $La^{3+}$, $Ce^{3+}$, $Pr^{3+}$, $Nd^{3+}$, $Pm^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$ and $Lu^{3+}$ are preferred. As the complex ions, $WO_4^{2-}$, $MoO_4^{2-}$, $VO_4^{3+}$, $Pt(CN)_4^{2-}$ and $WO_6^{6-}$ are preferred. When the optical fiber is added with at least one of these ions, the reflected signal light can be amplified at a high amplification factor. Further, since these ions are easy to add to the optical fiber and accordingly, the optical fiber light amplifier manufacturing cost, that is, the optical tomograph manufacturing cost, can be lowered by the use of these ions. As the optical fiber light amplifiers, those having an optical fiber added with pigment may be also suitably used.

Figure 2:
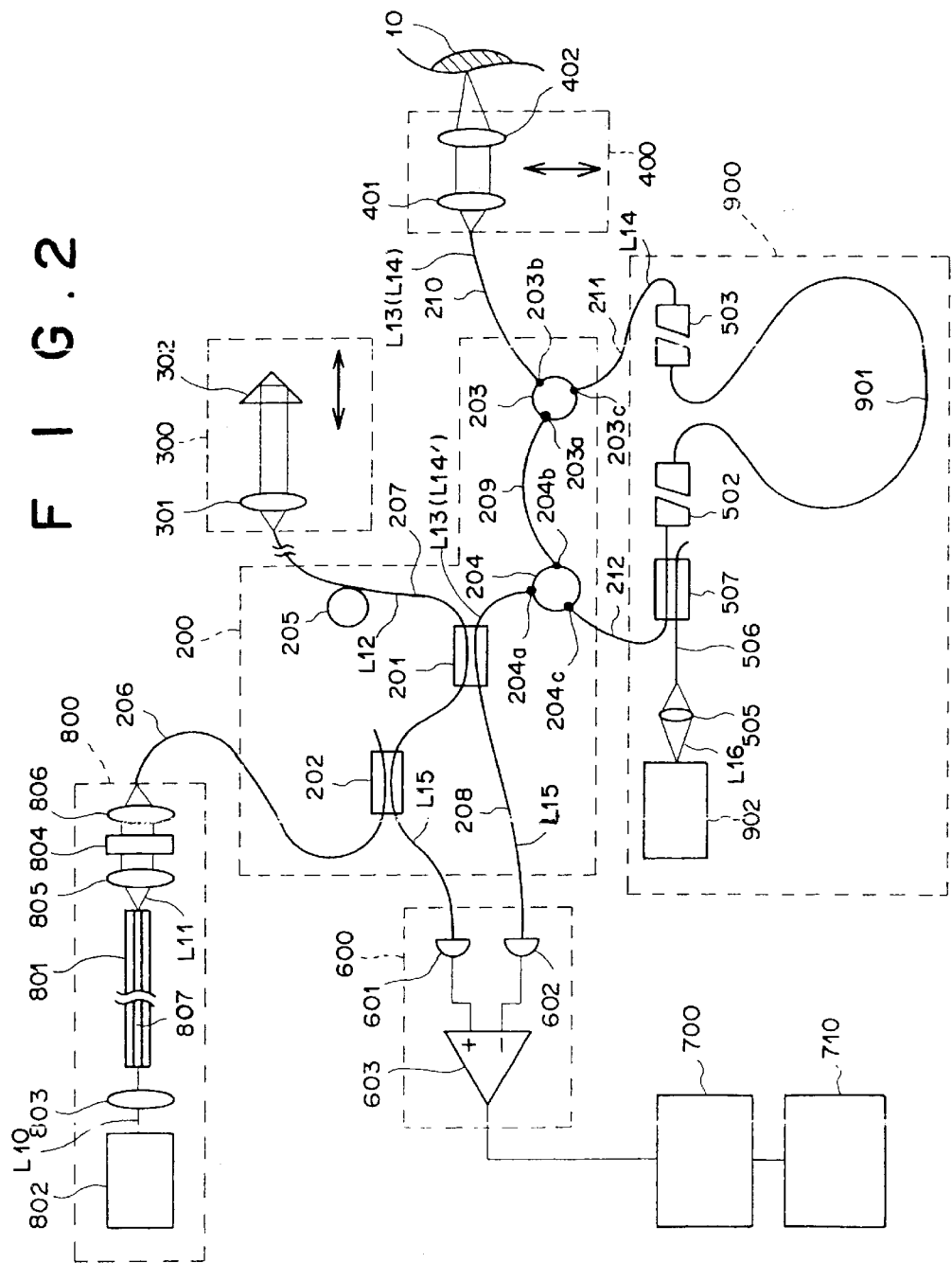
FIG. 2 is a schematic view showing an optical tomograph in accordance with a second embodiment of the present invention.

An optical tomograph in accordance with a second embodiment of the present invention will be described with reference to FIG. 2, hereinbelow. In FIG. 2, the elements analogous to those shown in FIG. 1 are given the same reference numerals and will not be described here.

In FIG. 2, the optical tomograph in accordance with the second embodiment of the present invention comprises a light source system 800 which emits a low coherence light beam L11, a fiber optical coupling system 200 which divides the low coherence light beam L11 emitted from the light source system 800 into a reference light beam L12 and a signal light beam L13, and couples the reference light beam L12 with the reflected signal light beam L13 reflected at an object as will be described in detail later, an optical path changing system 300 which changes the optical path length of the reference light beam L12, a scanning system 400 which causes the signal light beam L13 to scan an organic object 10, an optical fiber amplifier system 900 which amplifies the reflected signal light beam L14 (the signal light beam L13 reflected at a predetermined depth in the object 10) and emits amplified reflected signal light beam L14', a balancing difference detecting system 600 which detects the intensity of interference light beam L15 formed by the amplified reflected signal light beam L14' and the reference light beam L12, a signal processing system 700 which carries out heterodyne detection for obtaining the intensity of the reflected signal light beam L14 (the signal light beam L13 reflected at the predetermined depth in the object 10) on the basis of the intensity of the interference light beam L15 as detected by the balancing difference detecting system 600 and converts the intensity of the reflected signal light beam L14 into an image signal, and an image processing system 710 which reproduces a tomogram on the basis of the image signal obtained by the signal processing system 700.

The light source system 800 comprises a fiber laser 801 which emits the low coherence light beam L11 which is 800 nm in central wavelength and 200 nm in spectral width, a semiconductor laser 802 which emits a laser beam of 660 nm as an exciting light beam L10 for exciting the fiber laser 801, a lens 803 which converges the exciting light beam L10 on the light inlet end face of the fiber laser 801, an exciting light cut filter 804 which cuts light shorter than 700 nm in wavelength band and a pair of lenses 805 and 806 which condense the low coherence light beam L11 emitted from the fiber laser 801.

The fiber laser 801 is an optical fiber having a core 807 and pigment which absorbs the exciting light beam L10 and emits light. When the exciting light beam L10 enters the fiber laser 801, the fiber laser 801 emits the low coherence light beam L11 which is 800 nm in central wavelength and 200 nm in spectral width.

The optical fiber amplifier system 900 comprises a fiber optic amplifier 901 which amplifies a light beam input into the amplifier 901 when it is in an excited state, a pair of optical fiber connectors 502 and 503 connected at opposite ends of the amplifier 901, a semiconductor laser 902 which emits a laser beam of 660 nm as an exciting light beam L16 for the fiber optic amplifier 901, a condenser lens 505 which condenses the exciting light beam L16, an optical fiber 506 which introduces the exciting light beam L16 into the optical fiber 212 by way of a fiber optic coupler 507. The fiber optic amplifier 901 comprises an optical fiber whose core is added with the same pigment as that added to the core of the fiber laser 801.

Operation of the optical tomograph in accordance with this embodiment will be described, hereinbelow.

The exciting light beam L10 emitted from the semiconductor laser 802 is condensed by the lens 803 and introduced into the core 807 of the fiber laser 801.

The exciting light beam L10 is absorbed by the pigment added to the core 807 while it is propagating through the core 807. By absorbing the exciting light beam L10, the pigment shifts from a ground state to an excited state. Then the pigment returns to the ground state through thermal relaxation and/or light emission. Since the fiber laser 801 has no resonator, light emitted from the respective pigment particles propagates through the core without correlation and emanates through the light outlet end face of the fiber laser 801 as spontaneous emission. The spontaneous emission is low coherence light having spectral properties depending upon the emission spectrum of the pigment added to the core 807 and the transmitting properties of the fiber laser 801. Further, the intensity of the low coherence light L11 depends upon the intensity of the exciting light beam L10 and the amount of the pigment added to the core 807. That is, by selecting the intensity of the exciting light beam L10, the kind and amount of the pigment to be added to the core 807 and the length of the fiber laser 801, the center wavelength, the spectral width and the intensity of the low coherence light L11 can be controlled.

The low coherence light beams L11 at a wavelength of 800 nm emitted from the fiber laser 801 is collimated by the lens 805, removed with the exciting light L10 by the filter 804, is condensed by the lens 806 and caused to enter the optical fiber 206.

Operation of the optical fiber amplifier system 900 will be described here. The exciting light beam L16 at 660 nm emitted from the semiconductor laser 902 is condensed by the lens 505 and introduced into the optical fiber 506. The exciting light beam L16 is further introduced into the optical fiber 212 at the fiber optic coupler 507 and is introduced into the fiber optical amplifier 901 by way of the optical fiber connector 502. The exciting light beam L16 is absorbed by the pigment added to the core of the fiber optic amplifier 901 while it is propagating through the fiber optic amplifier 901.

By absorbing the exciting light beam L16, the pigment shifts from a ground state to an excited state. When the reflected signal light beam L14 enters the fiber optic amplifier 901 through one end thereof and propagates through the fiber optic amplifier 901 in the excited state, light in the same phase as the reflected signal light beam L14 is emitted in stimulated emission and the pigment returns to the ground state. Such stimulated emission is repeated and amplified reflected signal light beam L14' is emitted through the other end of the fiber optic amplifier 901. That is, since the amplified reflected signal light beam L14' is a signal in the same phase as the reflected signal light beam L14, optical tomographic image data can be obtained from the interference light beam L15 obtained by causing the reference light beam L12 and the amplified reflected signal light beam L14' to interfere with each other. Though spontaneous emission occurs together with the stimulated emission in the fiber optic amplifier 901, light emitted by the spontaneous emission is random in phase and does not interfere with the reference light beam L12. That is, the light emitted by the spontaneous emission does not adversely affect detection of the optical tomographic image.

By thus measuring the intensity of the interference light beam L15 obtained by causing the amplified reflected signal light beam L14' to interfere with the reference light beam L12, the same effect as in the first embodiment can be obtained.

Further, in this particular embodiment, the fiber optic amplifier 901 is added with pigment which can amplify light near to 800 nm in wavelength and accordingly, the reflected signal light beam L14 can be effectively amplified.

In order to obtain optical tomographic image data at a desired depth of the object, it is optimal that the signal light beam and the reference light beam interfere with each other only when the optical path length of the former perfectly coincides with that of the latter. However, actually, interference occurs when the difference in the optical path length between the signal light beam and the reference light beam is not larger than the coherence length of the light source. That is, resolution in low coherence interference depends on the coherence length of the light source.

Generally, when the wavelength distribution of the light source is a Gaussian distribution, the coherence length $\Delta L$ of the light source is given by formula $$\Delta L = (2/\pi)\cdot \ln 2 \cdot (\lambda c/\Delta\lambda)$$

wherein $\lambda c$ represents the central wavelength and $\Delta\lambda$ represents the spectral width.

For example, when the light source is the SLD employed in the first embodiment where the central wavelength is 780 nm and the spectral width is 20 nm, the coherence length $\Delta L$ is about 14 $\mu$m.

In the second embodiment, where the light source is the fiber laser 801 which emits light 800 nm in central wavelength and 20 nm in spectral width, the coherence length $\Delta L$ is about 1.4 $\mu$m and an optical tomogram can be obtained at high resolution.

In place of the fiber optic amplifier 901 added with pigment, a fiber optic amplifier added with ion selected from the group consisting of transition metal ions, rare earth element ions and complex ions. As the transition metal ion, $Ti^{4+}$, $Cr^{3+}$, $Mn^{4+}$, $Mn^{2+}$ and $Fe^{3+}$ are preferred. As the rare earth element ions, $Sc^{3+}$, $Y^{3+}$, $La^{3+}$, $Ce^{3+}$, $Pr^{3+}$, $Nd^{3+}$, $Pm^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$ and $Lu^{3+}$ are preferred. As the complex ions, $WO_4^{2-}$, $MoO_4^{2-}$, $VO_4^{3+}$, $Pt(CN)_4^{2-}$ and $WO_6^{6-}$ are preferred. When the fiber optic amplifier is added with at least one of these ions, the reflected signal light can be amplified at a high amplification factor. Further, since these ions are easy to add to the optical fiber and accordingly, the optical fiber light amplifier manufacturing cost, that is, the optical tomograph manufacturing cost, can be lowered by the use of these ions.

Though, in the embodiments described above, the frequency of the reference light beam is shifted by the piezo-element 205, a frequency difference between the reference light beam and the signal light beam may be generated in other manners. For example, the frequency of the signal light beam maybe shifted in place of the reference light beam or the frequencies of both the reference light beam and the signal light beam maybe shifted.

What is claimed is:

1. An optical tomograph which obtains a tomogram of an object by dividing a low coherence light beam into a signal light beam and a reference light beam, shifting the frequency of at least one of the signal light beam and the reference light beam so that the signal light beam and the reference light beam becomes different from each other in frequency, causing the signal light beam to impinge upon the object, causing the signal light reflected at a predetermined depth of the object to interfere with the reference light beam, and measuring the intensity of the obtained interference light, wherein the improvement comprises a light amplifier which amplifies said reflected signal light.

2. An optical tomograph as defined in claim 1 in which the light amplifier is a light amplifier with an optical waveguide.

3. An optical tomograph as defined in claim 2 in which the light amplifier is an optical fiber light amplifier.

4. An optical tomograph as defined in claim 3 in which the optical fiber light amplifier has an optical fiber added with at least one ion selected from the group consisting of transition metal ions, rare earth element ions and complex ions.

5. An optical tomograph as defined in claim 4 in which the optical fiber light amplifier has an optical fiber added with at least one ion selected from the group consisting of $Ti^{4+}$, $Cr^{3+}$, $Mn^{3+}$, $Mn^{3+}$, $Fe^{3+}$, $Sc^{3+}$, $Y^{3+}$, $La^{3+}$, $Ce^{3+}$, $Pr^{3+}$, $Nd^{3+}$, $Pm^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, $WO_4^{2-}$, $MoO_4^{2-}$, $VO_4^{3+}$, $Pt(CN)_4^{2-}$ and $WO^{66-}$.

6. An optical tomograph as defined in claim 3 in which the optical fiber light amplifiers has an optical fiber added with pigment.

7. An optical tomograph as defined in claim 1 in which the object is a part of an organic body and the low coherence light beam is from 600 nm to 1700 nm inclusive in wavelength.

8. The optical tomograph of claim 1 wherein the reflected light is amplified prior to interference with the reference light.

9. The optical tomograph of claim 1 comprising an optical fiber amplifier system wherein said amplifier system comprises:

a fiber optic amplifier which amplifies a light beam input into said amplifier when said light beam is in an excited state;

a pair of optical fiber connectors connected at opposite ends of said amplifier; and a laser emitting an exciting light beam.

10. The optical tomograph of claim 9, wherein said amplifier system further comprises:

a condensor lens wherein said condensor lens condenses the exciting light beam emitted from said laser; and an optical fiber wherein said optical fiber introduces said exciting light beam into a reflected signal carrying optical fiber by way of a fiber optic coupler.

11. An optical tomograph as described in claim 6, wherein said pigment forms population inversion between energy bands in accordance with the signal light to be amplified.

12. An optical tomograph according to claim 1 comprising a balancing difference detecting system wherein said balancing difference detecting system comprises:

at least two photodetectors wherein said photodetectors detect the intensity of an interference light beam; and a differential amplifier, wherein said differential amplifier adjusts input balance of detecting values of said photodetectors to cancel noise and drift components and amplifies the difference.

13. An optical tomograph according to claim 1, wherein the object is a part of an organic body and the low coherence light beam is from 600 nm to 1400 nm inclusive in wavelength.

* * * * *